(12) United States Patent
Varila

(10) Patent No.: US 9,095,206 B2
(45) Date of Patent: Aug. 4, 2015

(54) TOOTHBRUSH HEAD

(71) Applicant: Reijo Varila, Helsinki (FI)

(72) Inventor: Reijo Varila, Helsinki (FI)

(*) Notice: Subject to any disclaimer, the term of this patent is extended or adjusted under 35 U.S.C. 154(b) by 0 days.

(21) Appl. No.: 13/794,860

(22) Filed: Mar. 12, 2013

(65) Prior Publication Data
US 2013/0326833 A1 Dec. 12, 2013

Related U.S. Application Data

(60) Provisional application No. 61/744,676, filed on Jun. 11, 2012.

(30) Foreign Application Priority Data

Nov. 26, 2012 (FI) .................................... 20126243

(51) Int. Cl.
*A46B 7/06* (2006.01)
*A46B 13/02* (2006.01)
*A61C 17/22* (2006.01)
*A46B 9/02* (2006.01)

(52) U.S. Cl.
CPC . *A46B 7/06* (2013.01); *A46B 9/025* (2013.01); *A46B 9/026* (2013.01); *A46B 13/02* (2013.01); *A61C 17/222* (2013.01)

(58) Field of Classification Search
CPC ......... A46B 9/04; A46B 13/02; A61C 17/222
USPC ..................................................... 15/22.1, 28
See application file for complete search history.

(56) References Cited

U.S. PATENT DOCUMENTS

| D94,303 | S | * | 1/1935 | Hadley | D4/111 |
|---|---|---|---|---|---|
| 4,619,009 | A | * | 10/1986 | Rosenstatter | 15/29 |
| 5,467,495 | A | * | 11/1995 | Boland et al. | 15/28 |
| D483,183 | S | * | 12/2003 | De Salvo | D4/101 |
| 6,892,413 | B2 | * | 5/2005 | Blaustein et al. | 15/22.2 |
| D621,158 | S | * | 8/2010 | Driesen et al. | D4/101 |
| 7,788,756 | B2 | * | 9/2010 | Kraemer | 15/28 |
| 8,166,601 | B2 | * | 5/2012 | Brown et al. | 15/201 |

* cited by examiner

*Primary Examiner* — Randall Chin
(74) *Attorney, Agent, or Firm* — Seppo Laine Oy

(57) ABSTRACT

The present invention relates to a replacement brush head for an electromagnetic driven toothbrush and to a method of manufacturing such a brush head. The brush head includes a bristle carrier, where the bristle carrier has blind-end holes in which a plurality of tooth cleaning bristles can be fixedly attached. The bristles are arranged in inwardly centered rows, one behind the other. Bristles in outer rows are arranged in groups on both sides of the bristle carrier. Bristle groups are arranged with an outward leaning angle for efficient cleaning of the tooth neck area and gum pockets. Bristles in the inner rows can be shorter than the ones in the outer rows.

9 Claims, 8 Drawing Sheets

TOOTHBRUSH HEAD

FIELD OF INVENTION

The present invention generally relates to replacement brush heads, for example for use with an electromagnetic assembly. Additionally, a method of manufacture of the same is described herein.

BACKGROUND OF THE INVENTION

Plaque is the main cause to gingivitis and other gum diseases. It is a sticky material made of bacteria, mucus, and food debris and deposits particularly in the grooves and gum pockets evolved between the gum and teeth. Being concealed, technical level, conventional tooth brushes with right-angle bristles block rather than remove it when brushing the teeth. What is needed is a brush which is designed to remove plaque buildup at the neck of the tooth.

SUMMARY OF THE INVENTION

It is an object of the present invention to provide a toothbrush head. In particular, a toothbrush head for use as a replaceable toothbrush head of an electronic toothbrush.

It is an aspect of the present invention to provide a toothbrush head comprising a brush head housing coupled to a brush head shaft, a movable bristle carrier coupled to a pivoting axle of the brush head housing, and a mechanical linkage assembly coupled to the pivoting axle.

Additionally, the bristle carrier may contain a plurality of tooth cleaning elements which form bristle tufts, where a first portion of the bristle tufts are formed in to bristle tuft groups in a the outermost row(s) of a plurality of patterned rows, the bristle tuft groups being located on opposite sides of the bristle carrier on the brush head.

Furthermore, it is an aspect of certain embodiments for at least two of the bristle tuft groups in the outermost row(s) are disposed at a pivoting angle of between 5° and 45°, preferably between 20° and 30° off of a median line of the bristle carrier.

Still yet it is an aspect of certain embodiments for the median line of the bristle carrier to be disposed ±0° to 45°, for example 25°, from perpendicular from the longitudinal axis of the brush head shaft. Particularly, wherein the median line is disposed perpendicular to the longitudinal axis.

Furthermore, it is an aspect of certain embodiments that the bristle tuft groups are disposed in an outward leaning angle compared to a central axis of the pivoting axle. For example, wherein the outward leaning angle is between 5° and 45° and preferably between 15° and 25°.

The bristle tufts may have a round cross sectional shape, or other effective cross sectional shape. The first bristle tufts can also be at least 1.5× longer, preferably between 2× and 3× longer than the second bristle tufts.

Additionally, there is described herein a method of manufacturing the same.

In particular it is intended to improve the brushing efficiency of the teeth neck areas and gums.

DETAILED DESCRIPTION OF EXEMPLARY EMBODIMENTS

Figure 1A:
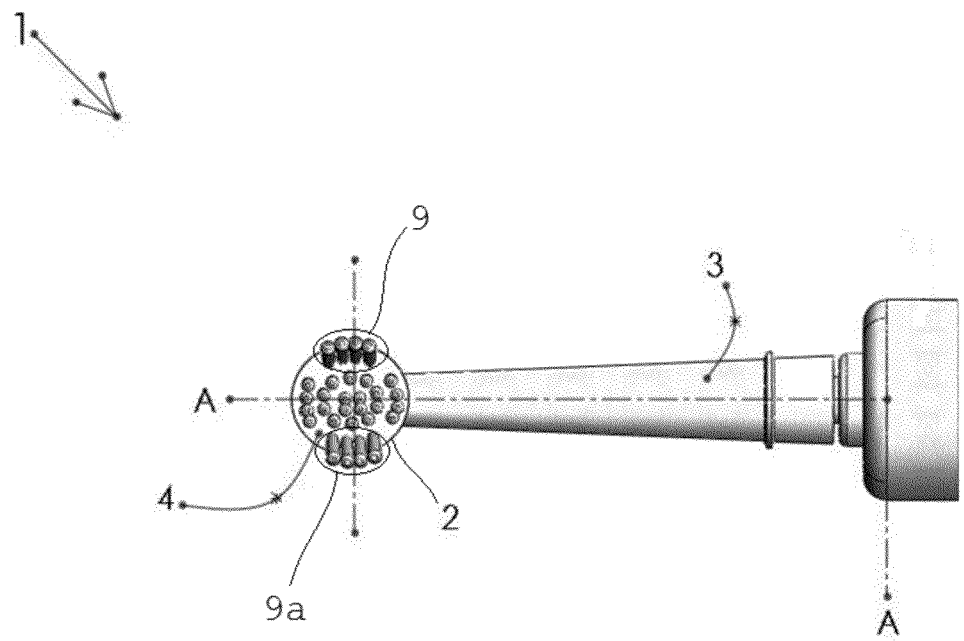
FIG. 1A shows a perspective top view of an electromagnet driven toothbrush with a brush head according to an embodiment of the present invention.

The present invention generally relates to a replacement toothbrush head for electric toothbrushes. According to certain embodiments, the toothbrush head may comprise, or consist of, some or all of the following elements; a driving electromagnet assembled in a toothbrush head 1, a brush head shaft 3, a brush head housing 2 comprising a bottom portion with a pivoting axle 5 in the centre and a movable bristle carrier 4 for carrying tooth cleaning bristles, a moveable bristle carrier 4 connected and/or coupled to a central pivoting axle 5; a brush head bottom member 8 fixedly connected to and/or coupled to a brush head shaft 3 and said brush head shaft 3 fixedly connected and/or coupled to said brush head housing 2; a brush head shaft 3 including a mechanical linkage assembly 6; a mechanical linkage assembly 6 connected to a movable bristle carrier 4 and an electromagnetic drive such that the bristle carrier 4 can pivot around a brush head pivoting axle 5 when the electromagnet is actuated.

The bristle carrier 4 can have blind-end bores in which a plurality of tooth cleaning bristles or other tooth cleaning elements can be fixedly attached. Examples of several types of tooth cleaning elements configured in to bristle tufts can be seen, for example, in FIGS. 9A-9D. The bristles and/or other tooth cleaning elements can be arranged into bristle tufts 7 & 7a each containing a plurality of the bristles or other tooth cleaning elements.

Figure 1B:
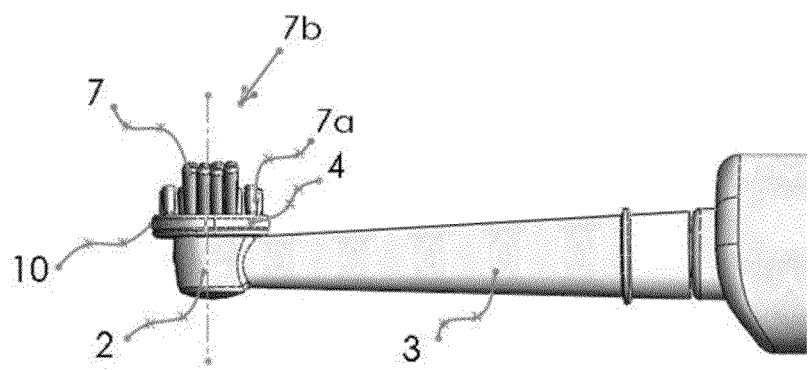
FIG. 1B shows a perspective side view of the electromagnet driven toothbrush of FIG. 1A.

FIGS. 1A and 1B show an example of a toothbrush head 1 according to the present invention. The toothbrush head 1 comprises a brush head housing 2, a brush head shaft 3 and a moveable bristle carrier 4. The moveable bristle carrier 4 has an outer contour 10 which is shown as a circle. The outer contour 10 of the bristle carrier may be elliptical or any other desired symmetric or asymmetric shape.

Figure 2:
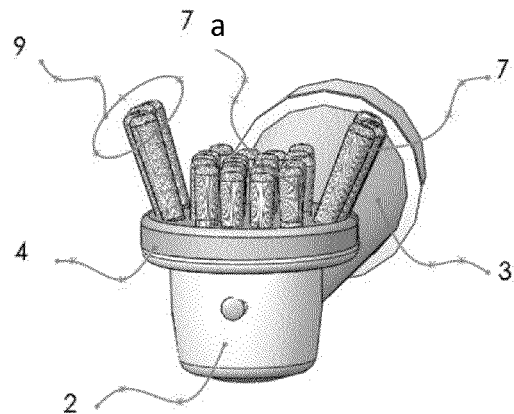
FIG. 2 is a perspective front view of the brush head of FIG. 1 showing the bristle tufts on the bristle carrier. The outer row is arranged in groups containing one or more elongated tufts which can be used in order to provide improved cleaning of the gums and teeth neck area.

The bristle carrier 4 further comprises a brush assembly 7b having a first set of bristle tufts 7 and a second set of bristle tufts 7a. FIG. 2 shows another angle of the unit of FIGS. 1A and 1B. The first set of bristle tufts 7 are seen in two rows of bristle tuft groups 9 and 9a, and the second set of bristle tufts 7a are shown in four rows in-between groups 9 and 9a.

Figure 3:
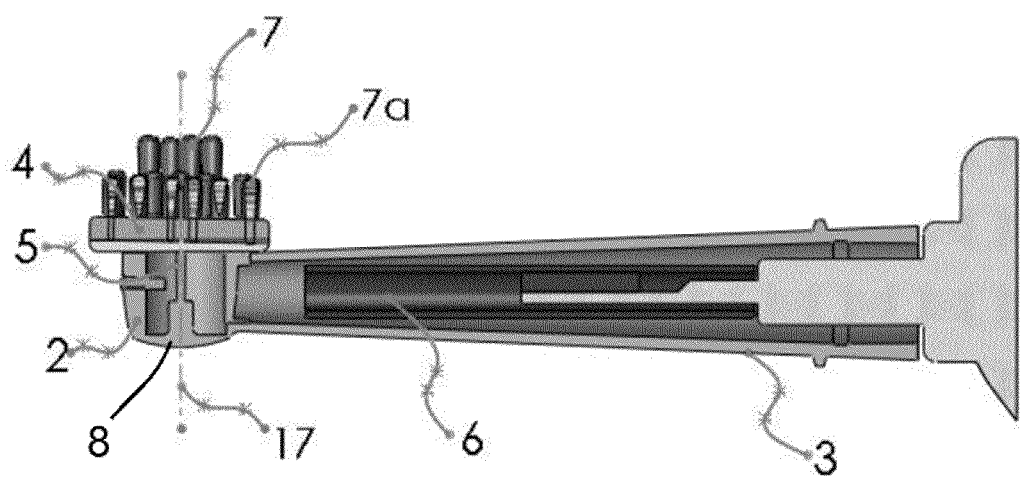
FIG. 3 is a sectional side view of the brush head taken along the cut line A-A in FIG. 1. The figure shows the brush head, brush head pivoting axle and bristle carrier pivoting mechanism.

FIG. 3 shows a cutaway of the unit 1 of FIG. 1 along the cut lines A-A. The toothbrush head unit 1 is shown comprising a mechanical linkage assembly 6 within the brush head shaft 3. The mechanical linkage assembly 6 is coupled to a pivoting axle 5 within the brush head housing 2. The brush head housing 2 may be an integral portion of the brush head shaft or they may be separate portions connected together during a manufacturing process. The pivoting axle 5 is orientated along a central axis 17 of the movable bristle carrier 4.

Figure 4:
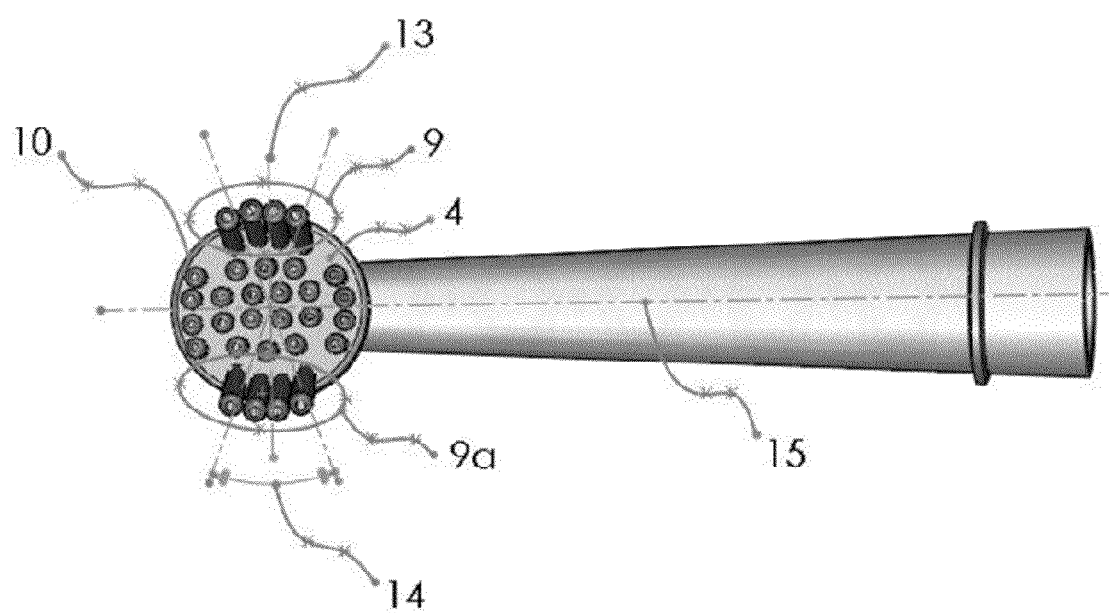
FIG. 4 is a top plan view of the brush head of FIG. 1 showing the location of the bristle tuft groups on the outer or second outer bristle tuft rows on the bristle carrier and arranged on both sides of the brush head shaft. The width of the bristle tuft groups on the outer row can be determined by the pivoting angle. The width may be narrower but should exceed more than 20% the width of the arch of the pivoting angle measured on the radius determined by the centre of the pivoting and the location of the bristle group on the bristle carrier.

FIG. 4 shows an arrangement of the bristle tufts on the bristle carrier with reference to the longitudinal axis 15 of the brush head shaft 3 and a median line 13 of the bristle carrier. The bristle tuft groups (9, 9a) in the outermost rows, which may be or may be considered as a single circular outer row, are disposed at a pivoting angle 14. The pivoting angle is shown as a displacement with regards to the median line 13. The pivoting angle 14 can be between 5° and 45° and is preferably between 20° and 30° off of a median line 13 of the bristle carrier 4.

Additionally, the median line 13 of the bristle carrier 4, which should divide the bristle carrier into two equal hemispheres, can be disposed ±0 to 45°, for example 25°, from perpendicular from the longitudinal axis 15 of the brush head shaft 3. However, the median line 13 is preferably perpendicular to the longitudinal axis 15.

Figure 5:
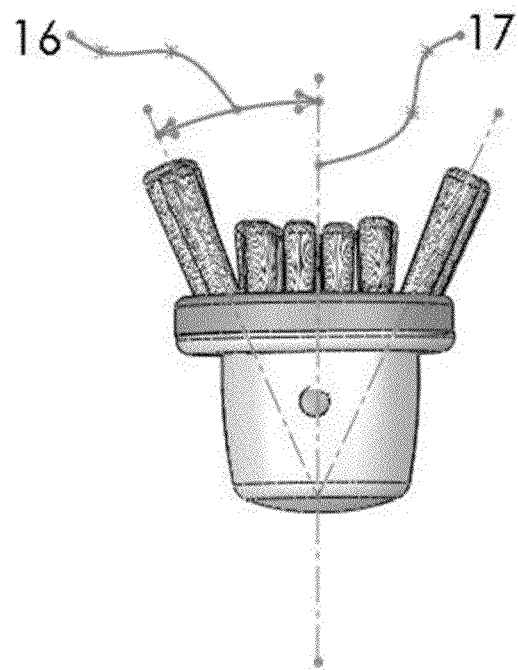
FIG. 5 is a front view of the brush head in FIG. 1 showing the outwardly inclined bristle tuft groups on both sides of the bristle carrier. As the bristle tuft groups are inclined into position where access to teeth neck and gum is optimized, these areas are more efficiently cleaned in brushing operation. This results in a decreased accumulation of plaque on the tooth neck.

FIG. 5 shows an example of a brush head housing 2 wherein the bristle tuft groups 9, 9a are disposed in an outward leaning angle 16 compared to a central axis 17 of the pivoting axle 5. The outward leaning angle 16 can be between 5° and 45° and preferably between 15° and 25°.

Figure 6:
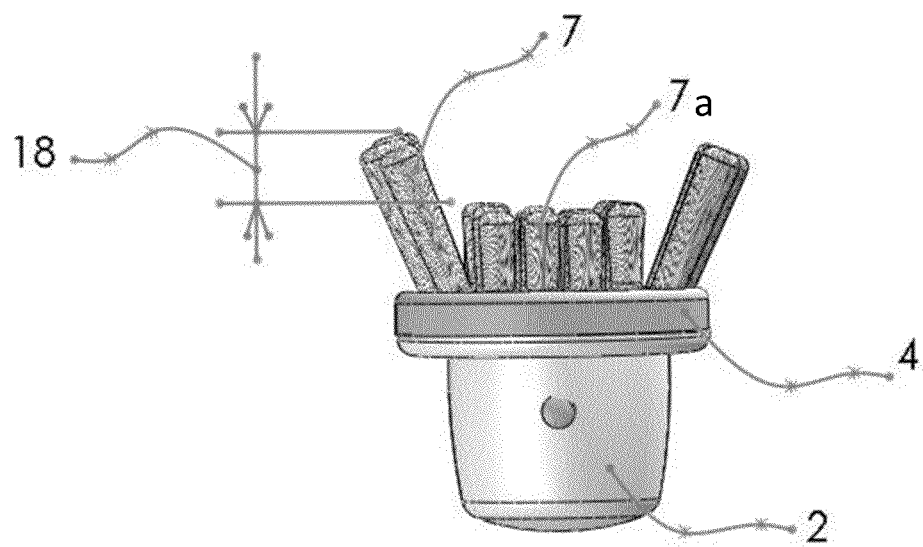
FIG. 6 is a perspective front view of the brush head in FIG. 1 showing the elongation of the bristles in the bristle tuft groups according to an example of the invention.

FIG. 6 shows the offset bristle length difference 18 between the lengths of the first and second set bristle tuft groups 7 and 7a. While first bristle tufts 7 can have some degree of variance, they can be, or can substantially be the same length. Similarly, while the second bristle tufts 7a can have some degree of variance, as shown in FIG. 6 for example, they can be, or can substantially be the same length. However, the first bristle tufts 7 should be longer than the second bristle tufts 7a.

The difference in length between the two groups can be considered as the true difference, i.e. when stood parallel to each other, or as an offset bristle length difference 18 as shown in FIG. 6 which takes in to consideration the disposition of the first bristle tufts 7 from the second bristle tufts 7a of the outward leaning angle 16. Either the true difference or the offset bristle length difference 18 between the first and second bristle tufts should be greater than 50%, i.e. the first bristle tufts 7 should be more than 1.5 times longer than the second bristle tufts 7a. Preferably, the offset bristle length difference should be 100-200%.

Figure 7A:
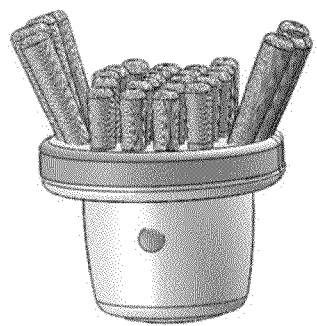
FIGS. 7A-C are perspective front views showing example variations of bristle tufts arrangement in the brush head of FIG. 1.
Figure 7B:
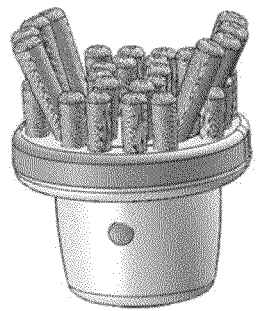
Figure 7C:
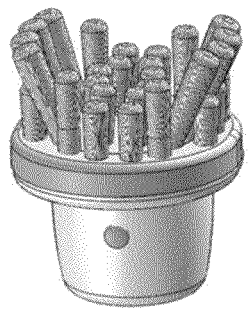

FIGS. 7A-7C shows several examples of bristle patterns on the bristle carrier 4. As can be seen, various arrangements according to the present invention can be implemented.

The bristles or other cleaning elements rows can follow a circular outer edge of the bristle carrier. Additionally, the bristle tufts in the outer, or second outer row can be arranged in groups containing one or more tufts of first and/or second bristle tufts 7, 7a. The bristle tuft groups 9 and 9a can form a semi arch with the length of the arch determined by the size of the pivoting angle.

Additionally, it is possible to arrange the first bristle tufts 7 in the outer or second outer row, advantageously in sectional groups covering each 10% to 40% of the total perimeter length of the row. Each of the sectional groups containing one or a plurality of individual bristle or other cleaning element tufts. Each bristle or other tooth cleaning element section formed by the bristle tufts can be located on the bristle carrier opposite to another similar section on the other side of the longitudinal axis of the brush head shaft.

Brushing efficiency is improved by having the tooth cleaning tuft groups in the outer or second outer row and arranged in an outward leaning angle so that the tufts are better able to reach the tooth neck area where most of plaque is deposited.

It should be understood from the design, and also proven in practice, that the shorter the inner row bristle tufts are in comparison with the outer row bristle tufts, the more the brushing efficiency is directed towards the outer rows. As bristle tufts in the outer rows, in accordance with this innovation, have been inclined outwards, they hence can better reach the tooth neck area and gum pockets where the plaque has been deposited during the day. The brushing efficiently of the outer row would reach the maximum if the inner bristles are cut all the way down. This would however reduce the overall brushing efficiency so an optimum between the overall brushing and tooth neck area brushing efficiencies is sought by adjusting the length of the middle row bristles accordingly.

Furthermore, there is described herein methods of manufacturing a toothbrush head in accordance with the present invention. According to such methods, a bristle carrier is manufactured having a multiplicity of bristles fastened thereto. The manufacturing process is simplified as it is possible to use existing tuft setting equipment for setting the bristle tufts.

Figure 8A:
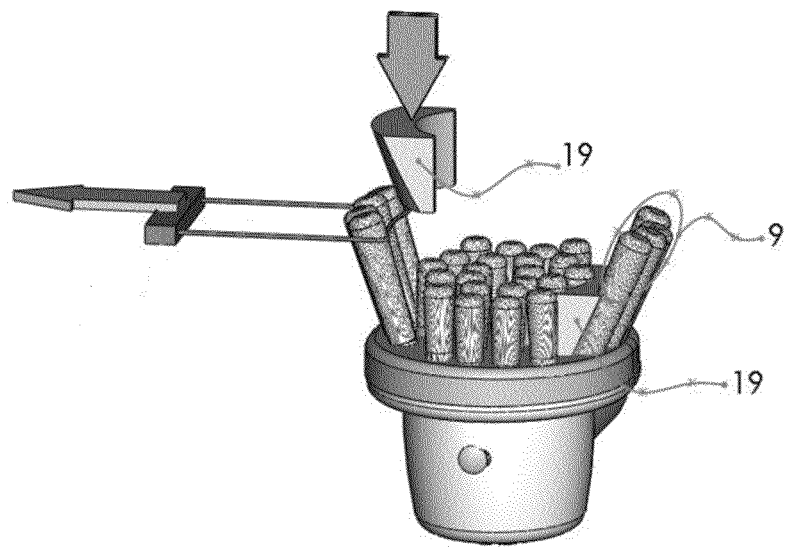
FIGS. 8A & B show two examples of manufacturing methods according to the present invention. For example, in FIG. 8A the bristle tuft groups are inserted on the outer row of the bristle carrier and are bent outwardly by a fixture. The position can then be secured by wedges glued in place between the bristle tuft groups and the next bristle row.
Figure 8B:
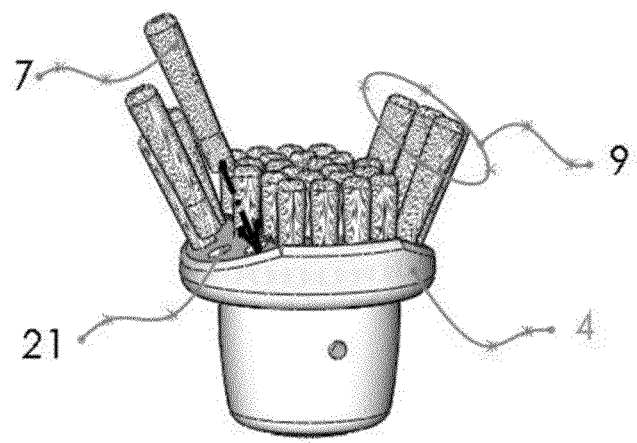
FIG. 8B shows another example method of inserting the bristle tufts into blind bores in the bristle carrier. The bores can be drilled in any desired angle.
Figure 9A:
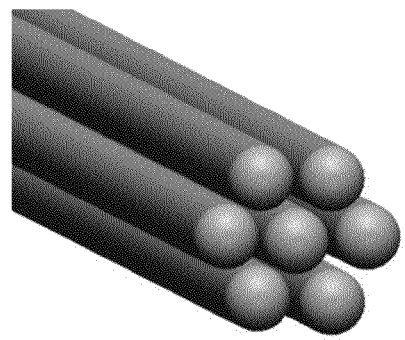
FIGS. 9A-D are examples of brush cleaning elements.
Figure 9B:
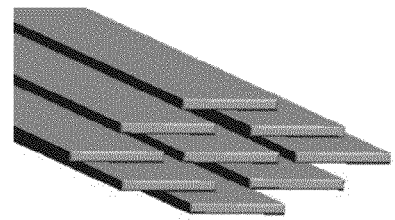
Figure 9C:
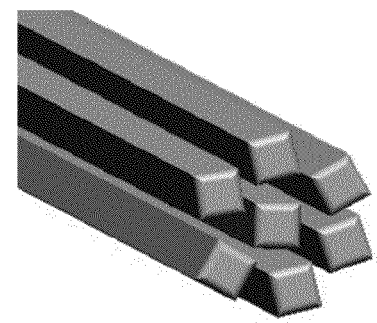
Figure 9D:
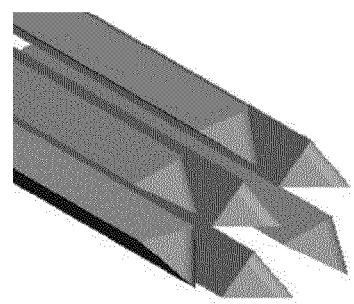

The bristle or other tooth cleaning element tufts are fastened to the bristle carrier for example either by using a metal plate anchor, by the same plastic material used for injection molding of the bristle carrier or any other method known by the art. Additionally, as shown in FIG. 8b, the bristles can be affixed in blind ended bores 21 drilled, or otherwise manufactured into the bristle carrier 4 at a desired outwardly leaning angle 16.

Figure 10:
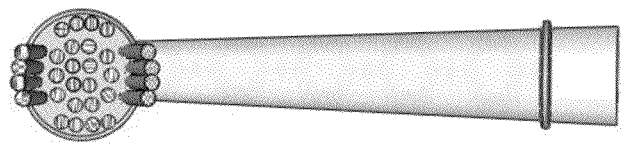
FIG. 10 shows a top plan view of a brush head.

It is to be understood that the embodiments of the invention disclosed are not limited to the particular structures, process steps, or materials disclosed herein, but are extended to equivalents thereof as would be recognized by those ordinarily skilled in the relevant arts. For example, FIG. 10 shows an arrangement of bristles in an alternative orientation with regards to the shaft. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

1—Toothbrush head
2—Brush head housing
3—Brush head shaft
4—Moveable bristle carrier
5—Pivoting axle
6—Mechanical linkage assembly
7—First bristle tufts
7a—Second bristle tufts
7b—Brush assembly
8—Brush head bottom member
9 & 9a—Bristle tuft groups
10—Outer contour of the bristle carrier
13—Median line of the bristle carrier
14—Pivoting angle
15—Longitudinal axis of the brush head shaft
16—Outward leaning angle
17—Central axis of the pivoting axle
18—Offset bristle length difference
19—Wedge
21—Blind ended bores

The invention claimed is:

1. A toothbrush head, comprising;
a brush head housing coupled to a brush head shaft,
a movable bristle carrier coupled to a pivoting axle of the brush head housing, and
a mechanical linkage assembly coupled to the pivoting axle,
wherein the bristle carrier contains a plurality of tooth cleaning elements which form bristle tufts, a first portion of the bristle tufts are formed into bristle tuft groups in an outermost row(s) of a plurality of patterned rows, the bristle tuft groups being located on opposite sides of the longitudinal axis of the brush head shaft,
wherein at least two of the bristle tuft groups in the outermost row(s) are disposed at a pivoting angle of between 5° and 45° off of a median line of the bristle carrier,
wherein the bristle tuft groups are disposed in an outward leaning angle compared to a central axis of the pivoting axle,
wherein the first portion of the bristle tufts is at least 1.5× longer than a second portion of the bristle tufts, and
wherein wedges are glued in place between the first portion of the bristle tufts and the second portion of the bristle tufts.

2. A toothbrush head according to claim 1, wherein the median line of the bristle carrier is disposed ±0 to 45° from perpendicular from the longitudinal axis of the brush head shaft.

3. A toothbrush head according to claim 1, wherein the median line of the bristle carrier is disposed perpendicular to the longitudinal axis of the brush head shaft.

4. A toothbrush head according to claim 1, wherein the outward leaning angle is between 5° and 45°.

5. A toothbrush head according to claim 1, wherein the bristle tufts have a round cross sectional shape.

6. A toothbrush head according to claim 1, wherein the bristle carrier has a circular or elliptical shape and the bristle tuft groups follow the outer contour of the bristle carrier.

7. A toothbrush head according to claim 1, wherein the bristle groups form pairs on the outermost row(s) and on opposite sides of the longitudinal axis.

8. A toothbrush head according to claim 1, wherein the bristle tuft groups each have an equal number of bristle tufts equally divided on either side of the median line and within the pivoting angle.

9. A toothbrush head according to claim 1, wherein the second portion of the bristle tufts form a plurality of rows, at least some of the rows between the outermost row(s) of the first portion of the bristle tufts.

* * * * *